(12) United States Patent
Bees

(10) Patent No.: US 6,247,673 B1
(45) Date of Patent: Jun. 19, 2001

(54) COUNTERWEIGHT FOR STANDS

(75) Inventor: Bryan Bees, Balgach (CH)

(73) Assignee: Leica Microsystems AG (CH)

( * ) Notice: Subject to any disclaimer, the term of this patent is extended or adjusted under 35 U.S.C. 154(b) by 0 days.

(21) Appl. No.: 09/242,419

(22) PCT Filed: Jun. 16, 1998

(86) PCT No.: PCT/EP98/03614

§ 371 Date: Mar. 12, 1999

§ 102(e) Date: Mar. 12, 1999

(87) PCT Pub. No.: WO99/01693

PCT Pub. Date: Jan. 14, 1999

(30) Foreign Application Priority Data

Jun. 30, 1997 (CH) .................................................... 1566/97

(51) Int. Cl.[7] .................................................. F16L 3/00
(52) U.S. Cl. .................................. 248/123.11; 248/292.11
(58) Field of Search ........................ 248/122.1, 123.11, 248/123.2, 280.11, 292.11, 297.11, 648, 289.11, 299.11, 364, 910; 403/112, 113, 116, 117; 359/384, 368, 382

(56) References Cited

U.S. PATENT DOCUMENTS

| | | | |
|---|---|---|---|
| 2,729,473 | * 1/1956 | Warshawsky | 248/289.11 |
| 3,358,957 | 12/1967 | Lindenmuth | 248/279.1 |
| 3,790,773 | * 2/1974 | Sapper | 248/123.11 |
| 3,918,672 | * 11/1975 | Torn et al. | 248/447 |
| 4,515,333 | 5/1985 | Pugh et al. | 248/122 |
| 4,523,732 | 6/1985 | Biber et al. | 248/123.1 |
| 4,821,159 | * 4/1989 | Pike | 362/285 |
| 5,213,293 | 5/1993 | Muentener et al. | 248/123.1 |
| 5,257,998 | 11/1993 | Ota et al. | 606/130 |
| 5,288,043 | 2/1994 | Tigliev | 248/123.1 |
| 5,448,464 | * 9/1995 | Moss | 362/401 |
| 5,477,443 | * 12/1995 | Cvek | 362/413 |
| 5,630,566 | * 5/1997 | Case | 248/122.1 |
| 5,655,741 | * 8/1997 | Watkins | 248/289.11 |
| 5,695,279 | * 12/1997 | Sonnleitner | 362/419 |

FOREIGN PATENT DOCUMENTS 3808327    9/1988 (DE) .

* cited by examiner

*Primary Examiner*—Leslie A. Braun
*Assistant Examiner*—Gwendolyn Baxter
(74) *Attorney, Agent, or Firm*—Simpson, Simpson & Snyder, L.L.P.

(57) ABSTRACT

The invention relates to a support stand with a carrying arm (3), a standard (4), and a support stand foot (6), where a functional housing (5) serving as counterbalance is secured to the standard (4). The dimensions of the foot (6) of the support stand are such that said foot exhibits a preferred direction of support (15) that affords increased security against tipping and exhibits a permitted area of support lateral to the preferred direction of support (15). The swivel capability of the carrying arm (3) on a horizontal plane is limited by a stop (9), in such a way that the carrying arm (3) cannot swivel into a position perpendicular to the direction of support and cannot swivel outside of the permitted area of support.

11 Claims, 1 Drawing Sheet

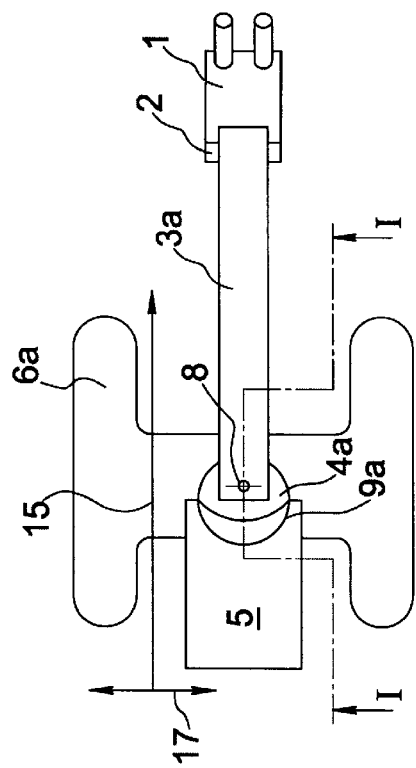
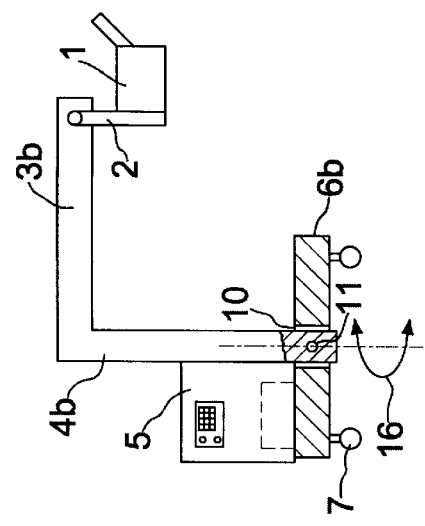
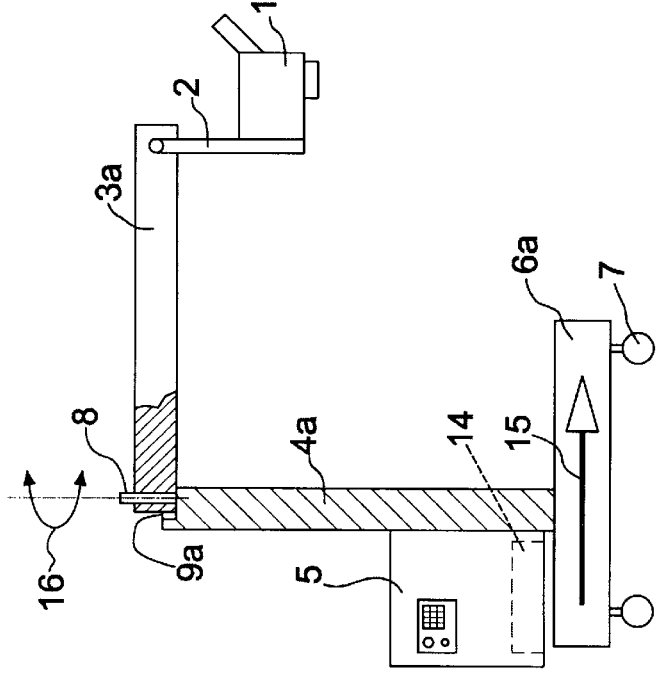
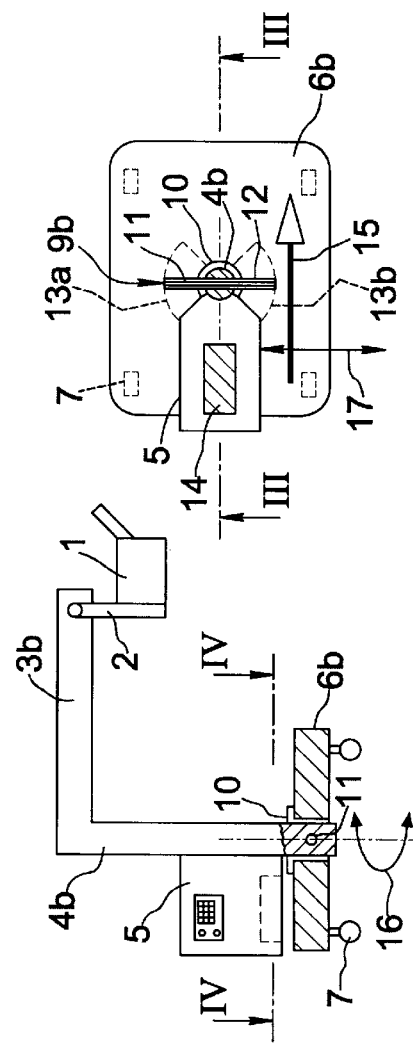

COUNTERWEIGHT FOR STANDS

BACKGROUND OF THE INVENTION

The invention relates to a support stand, particularly a support stand for an operating microscope. Alongside expensive structures with counterbalances for support stands, there are also simpler support structures in the area of operating microscopy which manage without vertical parallel supports and which use a gas-loaded spring, or the like, as a counterweight for holding the operating microscope in balance. Reference is made in this regard to the applicant's patent U.S. Pat. No. 5,213,293. This kind of relatively simple support stand is designed in such a way that the stand foot has enough stability for the stand not to tip when conventional operating microscopes are employed.

Known from U.S. Pat. No. 5,257,998 is a support stand for a stereotaxis system that exhibits a support stand foot and a standard assigned to it. A carrying arm with a counterbalance is secured to the stand. The counterbalance is equipped as a functional housing containing different electrical structural components. The large swivel area of the stand gives the foot a symmetrical design, and the foot is consequently very large and heavy.

SUMMARY OF THE INVENTION

The invention is based on the problem of modifying the stand design in a way that permits it to carry heavier weights in the area of the load, particularly the area of the operating microscope, and/or to give the foot of the stand a lighter design.

A certain problem arises with stand feet: the further the feet project laterally into space, the more they hinder the personnel. An attempt is therefore made to limit the width of the feet. A further task of the present invention is to meet the need for a lighter foot.

These problems are solved by the features indicated in the characterizing portion of patent claim 1.

The combination of features shown in claim 1 yields a design that is simple, provides a practical counterbalance, and exhibits a reduced tendency to tip. Elaborations of the invention emerge from the dependent claims. Together with the drawings, the specialist will see a novel stand design that does justice both to the problems addressed by the invention and the need to equip conventional stands with electronic equipment.

BRIEF DESCRIPTION OF THE DRAWINGS

The following description of the figures involves all the figures. Identical structural parts have identical reference numbers; different but functionally comparable parts have identical reference numbers but different secondary indices.

Shown are:

FIG. 1: a variation in side view, in which the carrying arm can be rotated around a swivel axis;

FIG. 2: a top view of the structure shown in FIG. 1;

FIG. 3: a variation of the same in side view;

FIG. 4: a section through the structure of FIG. 3 along line IV—IV; and

FIG. 5: a view similar to that of FIG. 3, showing a variation wherein an electronic control box is supported by a foot of the invention.

Not shown in the figures are certain supporting mechanisms like gas pressure springs or like, such as those known from the referenced U.S. Pat. No. 5,213,293. Express reference is therefore made to the content of this publication for the purpose of a more detailed design of the carrying arm support structure of the stand according to the invention. The design according to the invention is not restricted to such elaborations, however.

DETAILED DESCRIPTION OF THE PREFERRED EMBODIMENTS

The support stand according to the invention has a standard which bears a carrying arm 3a or 3 b. A control box 5 that is connected in rigid fashion to the standard 4a or 4b serves as a counterbalance for a weight mounted on the swivel arm, for example, an operating microscope 1. The control box 5 might contain, for example, electronic components, power supply equipment, any equipment needed for illumination, etc., and, if required, additional weights 14.

FIG. 1 shows an embodiment in which the carrying arm 3a can be rotated around a swivel axis 8 on the standard 4a, see the circular double arrow 6. A stop 9a limits the lateral mobility of the carrying arm 3a in both directions. This assures that the carrying arm 3a cannot swivel into a position that runs athwart the preferred direction of support 15 of the stand foot 6a. The foot 6a is designed in a way such that it offers comparatively little security against tipping in a direction perpendicular to the preferred support direction 15. This embodiment is cut along section I—I in FIG. 2.

FIG. 2 shows the structure of FIG. 1 in top view. It is clear from the figure that the foot 6a has an H shape and thus extends considerably further in the direction of support 15 than in the direction 17 perpendicular thereto. As compared to a square or a circle, the foot can thus have a light weight while providing an unlimited degree of security against tipping in the direction of support 15.

FIGS. 3 and 4 show a variant in which the carrying arm 3b and the standard 4b are rigidly connected in turning fashion. FIG. 3 shows a section along line III—III in FIG. 4. With this structure, the swivel movement suggested by the double arrow 16 on a horizontal plane is guaranteed by the rotating capability of the standard 4b within the foot 6b. To this end, the standard 4b is inserted into a hole in the foot 6b and is supported with respect to the foot by a support ring 10. At least one stop pin 11 slides within a stop groove 13 (13a, 13b) to limit the lateral swiveling movement of the standard 4b. Serving to mount the standard 4b within the foot 6b are, for example, mounting slits 12 which permit the standard 4b to sink into the foot 6b along with the stop pin(s) 11.

The two depicted variants do not show a potential swivel motion of the carrying arm 3a on a vertical plane. This kind of movement, and the structural measures required to execute it, are known to the specialist in a variety of ways. Reference is made, for example, to the already mentioned U.S. Pat. No. 5,213,293 and the applicant's support stand based on that publication.

The core of the present invention rests in the combination of a rigid counterbalance, specifically one containing functional parts, positioned on a standard, and a stop which limits the swivel motion of the carrying arm on a horizontal plane, ideally in symmetrical fashion relative to the preferred direction of support.

List of Reference Numerals 1 operating microscope
2 microscope support
3 a, b carrying arm
4 a, b standard 5 control box/housing
6 a, b stand foot
7 roller or supporting foot
8 swivel axis
9 a, b stop
10 support ring
11 stop pin
12 mounting slit
13 a, b stop groove
14 weights
15 preferred direction of support
16 double arrow
17 perpendicular direction

What is claimed is:

1. A support stand comprising:
    a foot elongated in a chosen direction of support;
    a standard extending only along a vertical axis from said foot;
    a carrying arm mounted on said standard, said carrying arm being rotatable in a horizontal plane about a swivel axis coinciding with said vertical axis of said standard;
    a functional housing secured to said standard such that the weight of said functional housing and any items therein has a line of action offset from said vertical axis of said standard to act as a counterbalance to said carrying arm and loads carried thereby; and
    stop means for preventing said carrying arm from being rotated to a position wherein said carrying arm extends in a direction generally perpendicular to said direction of support.

2. The support stand according to claim 1, wherein said standard and said carrying arm rotate together about said swivel axis, and said stop means acts between said standard and said foot.

3. The support stand according to claim 1, wherein said carrying arm rotates relative to said standard about said swivel axis, and said stop means acts between said carrying arm and said standard.

4. The support stand according to claim 1, further comprising an electronic power supply and control system enclosed by said housing for operating said stand.

5. The support stand according to claim 1, further comprising an electronic power supply and control system enclosed by said housing for operating a microscope supported by said stand.

6. The support stand according to claim 1, further comprising additional counterweight enclosed by said housing for counterbalancing said carrying arm and loads carried thereby.

7. The support stand according to claim 1, further comprising a spring for supporting said carrying arm.

8. The support stand according to claim 1, wherein said stop means defines a swivel area for said carrying arm which is symmetrical about said direction of support.

9. The support stand according to claim 1, wherein said foot extends further in said direction of support than in a direction perpendicular to said direction of support.

10. The support stand according to claim 1, wherein said housing is supported by said foot.

11. A surgical apparatus comprising, in combination:
    a support stand including a foot elongated in a direction of support, a standard extending vertically from said foot, a carrying arm connected to said standard, said carrying arm being rotatable in a horizontal plane about a swivel axis, a functional housing secured to said standard, and stop means for preventing said carrying arm from being rotated to a position wherein said carrying arm extends in a direction generally perpendicular to said direction of support; and
    a surgical microscope carried by said carrying arm.

* * * * *